(12) United States Patent
Kimbahune et al.

(10) Patent No.: US 11,432,779 B2
(45) Date of Patent: Sep. 6, 2022

(54) METHOD AND DEVICE FOR CAPACITIVE TOUCH PANEL BASED BIOSIGNAL MEASUREMENT

(71) Applicant: Tata Consultancy Services Limited, Mumbai (IN)

(72) Inventors: Sanjay Madhukar Kimbahune, Thane (IN); Sujit Raghunath Shinde, Thane (IN); Karan Bhavsar, Thane (IN); Arpan Pal, Kolkata (IN); Avik Ghose, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 161 days.

(21) Appl. No.: 16/823,415

(22) Filed: Mar. 19, 2020

(65) Prior Publication Data

US 2021/0169429 A1    Jun. 10, 2021

(30) Foreign Application Priority Data

Dec. 4, 2019   (IN) .............................. 201921050009

(51) Int. Cl.
*A61B 5/00*   (2006.01)
*G16H 50/20*   (2018.01)
(Continued)

(52) U.S. Cl.
CPC ........ *A61B 5/7475* (2013.01); *A61B 5/02444* (2013.01); *A61B 5/7203* (2013.01);
(Continued)

(58) Field of Classification Search
CPC ............ A61B 5/02405; A61B 5/02438; A61B 5/02444; A61B 5/6898; A61B 5/7203;
(Continued)

(56) References Cited

U.S. PATENT DOCUMENTS 10,254,877 B2   4/2019   Kim et al.
10,299,729 B2   5/2019   Wang et al.
(Continued)

FOREIGN PATENT DOCUMENTS

KR     10-1462283      11/2014
KR     2016-0061211    5/2016

OTHER PUBLICATIONS

Savage J. Ethnography and health care. BMJ. 2000;321(7273):1400-1402. doi: 10.1136/bmj.321.7273.1400 (Year: 2000).*

*Primary Examiner* — Mallika D Fairchild
*Assistant Examiner* — Shreya Anjaria
(74) *Attorney, Agent, or Firm* — Finnegan, Henderson, Farabow, Garrett & Dunner, LLP

(57) ABSTRACT

Many capacitive sensing based biosignal measurements methods exist, which are generic as they do not personalize biosignal measurement. Further, are do not provide device agnostic solutions. A method and system for capacitive touch panel based biosignal measurement is provided. The method senses a change in raw capacitance value of a capacitive touch panel. However, unlike existing methods that directly utilize the raw signal for biosignal measurements, the method disclosed derives a normalized signal by normalizing a raw signal corresponding to the change in raw capacitance of the capacitive touch panel. The normalization considers inter-relationships between a plurality of variables that affect the raw capacitance value such as a set of device specific parameters associated with the capacitive touch panel of the device, a set of ethnographic parameters, and metadata associated with the subject. Thus, method provides higher accuracy in biosignal measurement using capacitive touch panel based devices by personalizing the biosignal measurements.

9 Claims, 9 Drawing Sheets

(51) Int. Cl.
*A61B 5/024* (2006.01)
*G06F 3/044* (2006.01)

(52) U.S. Cl.
CPC ............ *A61B 5/725* (2013.01); *A61B 5/7267* (2013.01); *A61B 5/742* (2013.01); *G16H 50/20* (2018.01); *G06F 3/044* (2013.01)

(58) Field of Classification Search
CPC ..... A61B 5/725; A61B 5/7253; A61B 5/7267; A61B 5/742; A61B 5/7475; G06F 3/044; G16H 50/20
See application file for complete search history.

(56) References Cited

U.S. PATENT DOCUMENTS

| | | |
|---|---|---|
| 10,342,494 B2 | 7/2019 | Kim et al. |
| 2016/0228015 A1* | 8/2016 | Akhbardeh ............ A61B 5/302 |
| 2017/0027521 A1* | 2/2017 | Geva .................. A61B 5/02055 |
| 2017/0112445 A1* | 4/2017 | Wang ................... A61B 5/7475 |
| 2017/0246086 A1* | 8/2017 | Jain ....................... A61J 7/0481 |

* cited by examiner

METHOD AND DEVICE FOR CAPACITIVE TOUCH PANEL BASED BIOSIGNAL MEASUREMENT

PRIORITY CLAIM

This U.S. patent application claims priority under 35 U.S.C. § 119 to: Indian application no. 201921050009, filed on Dec. 4, 2019. The entire contents of the aforementioned application are incorporated herein by reference.

TECHNICAL FIELD

The embodiments herein generally relate to the field of biosignal measurements and, more particularly, to method and device for capacitive touch panel based biosignal measurement.

BACKGROUND

Handheld and wearable devices have been used widely for day to day health monitoring and screening. Initial monitoring of vital signs via contact and non-contact-based measurements using such wearable devices or handheld devices without need for clinical measurements has become increasingly popular. This non-clinical monitoring enables seamless health monitoring and alerting a subject at early stages of health fluctuations. Research and development has been carried out to make theses portable non-clinical measurements methods more accurate, reliable, cost efficient and power efficient. Various sensors have been tried and tested for these portable, handheld devices that enable capturing biosignals such as photoplethysmogram (PPG), electrocardiogram (ECG), to derive various parameters from the sensed biosignals. The parameters derived such as beat-to-beat interval, hear rate and the like, and are indicative of health condition of the subject. Monitoring vital signs using capacitive sensing is much more power efficient than optical measurements. Touch panels or touch screens of the devices have capacitive sensor arrays to sense the touch. The sensor capacitance depends on the dielectric constant of the surrounding medium and therefore, can be used to measure the dielectric properties of the biological tissue. Tissue permittivity determines the change in capacitance that is modeled as a parallel capacitor with capacitance determined by the tissue properties.

Many capacitive sensing based biosignal measurements methods exist, which are generic as they do not personalize biosignal measurement and are device specific solutions. However, it can be noted that change in capacitance of a touch panel, which is a measure of biosignal of the subject, is not standard or constant but is affected by characteristics associated with end user such as age, skin, sweat or moisture and other ethnographic parameters. Thus, non-consideration of such user dependent characteristics leads to error prone biosignal measurement. Further, these existing methods are device specific as change in capacitance is highly dependent on capacitive touch panel characteristics, which may vary from device to device.

SUMMARY

Embodiments of the present disclosure present technological improvements as solutions to one or more of the above-mentioned technical problems recognized by the inventors in conventional systems. For example, in one embodiment, a method for capacitive touch panel based bio-signal measurement is provided. The method comprising detecting a touch event performed by a subject on a capacitive touch panel of a device comprising an array of sensors by scanning the array at regular predefined time intervals. Further, obtaining a raw signal corresponding to change in a raw capacitance value generated by the capacitive touch panel on detection of the touch event. Further, deriving a normalized signal by normalizing the raw signal using a normalization model, wherein the normalization model derives the normalized signal based on inter-relationships between a plurality of variables that affect the raw capacitance value, wherein the plurality of variables comprise a) a set of device specific parameters associated with the capacitive touch panel of the device, b) a set of ethnographic parameters, and c) metadata associated with the subject. Furthermore, extracting from the normalized signal, a set first set of ore parameters associated with a primary biosignal among a plurality of biosignals corresponding to the subject in accordance to a capacitance signal to a biosignal conversion model. Thereafter, deriving a set second set of parameters associated with one or more secondary biosignals among the plurality of biosignals from the first set of parameters associated with the primary biosignal. Further, analyzing the first set of parameters associated with the primary biosignal and the second set of parameters associated with the secondary biosignals to determine health condition of the subject by comparing the analyzed one first set of parameters and the second set of parameters with corresponding subject specific standard values. Furthermore, displaying the analysis on the device indicating current health condition of the subject.

In another aspect, a device for capacitive touch panel based biosignal measurement. The device comprises a memory storing instructions; one or more Input/Output (I/O) interfaces; and one or more hardware processors coupled to the memory via the one or more I/O interfaces, wherein the one or more hardware processors are configured by the instructions to detect a touch event performed by a subject on a capacitive touch panel of a device comprising an array of sensors by scanning the array at regular predefined time intervals. Further, the one or more hardware processors are configured to obtain a raw signal corresponding to change in a raw capacitance value generated by the capacitive touch panel on detection of the touch event. Further, the one or more hardware processors are configured to derive a normalized signal by normalizing the raw signal using a normalization model, wherein the normalization model derives the normalized signal based on inter-relationships between a plurality of variables that affect the raw capacitance value, wherein the plurality of variables comprise a) a set of device specific parameters associated with the capacitive touch panel of the device, b) a set of ethnographic parameters, and c) metadata associated with the subject. Furthermore, the one or more hardware processors are configured to extract from the normalized signal, a first set of parameters associated with a primary biosignal among a plurality of biosignals corresponding to the subject in accordance to a capacitance signal to a biosignal conversion model. Thereafter, the one or more hardware processors are configured to derive a second set of parameters associated with one or more secondary biosignals among the plurality of biosignals from the first set of parameters associated with the primary biosignal. Further, the one or more hardware processors are configured to analyze the first set of parameters associated with the primary biosignal and the second set of parameters associated with the secondary biosignals to determine health condition of the subject by comparing the analyzed first set of parameters and the second set of parameters of with corresponding subject specific standard values. Furthermore, the one or more hardware processors are configured to display the analysis on the device indicating current health condition of the subject.

In yet another aspect, there are provided one or more non-transitory machine readable information storage mediums comprising one or more instructions, which when executed by one or more hardware processors causes a method for capacitive touch panel based bio-signal measurement. The method comprising detecting a touch event performed by a subject on a capacitive touch panel of a device comprising an array of sensors by scanning the array at regular predefined time intervals. Further, obtaining a raw signal corresponding to change in a raw capacitance value generated by the capacitive touch panel on detection of the touch event. Further, deriving a normalized signal by normalizing the raw signal using a normalization model, wherein the normalization model derives the normalized signal based on inter-relationships between a plurality of variables that affect the raw capacitance value, wherein the plurality of variables comprise a) a set of device specific parameters associated with the capacitive touch panel of the device, b) a set of ethnographic parameters, and c) metadata associated with the subject. Furthermore, extracting from the normalized signal, a set first set of ore parameters associated with a primary biosignal among a plurality of biosignals corresponding to the subject in accordance to a capacitance signal to a biosignal conversion model. Thereafter, deriving a set second set of parameters associated with one or more secondary biosignals among the plurality of biosignals from the first set of parameters associated with the primary biosignal. Further, analyzing the first set of parameters associated with the primary biosignal and the second set of parameters associated with the secondary biosignals to determine health condition of the subject by comparing the analyzed one first set of parameters and the second set of parameters with corresponding subject specific standard values. Furthermore, displaying the analysis on the device indicating current health condition of the subject.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
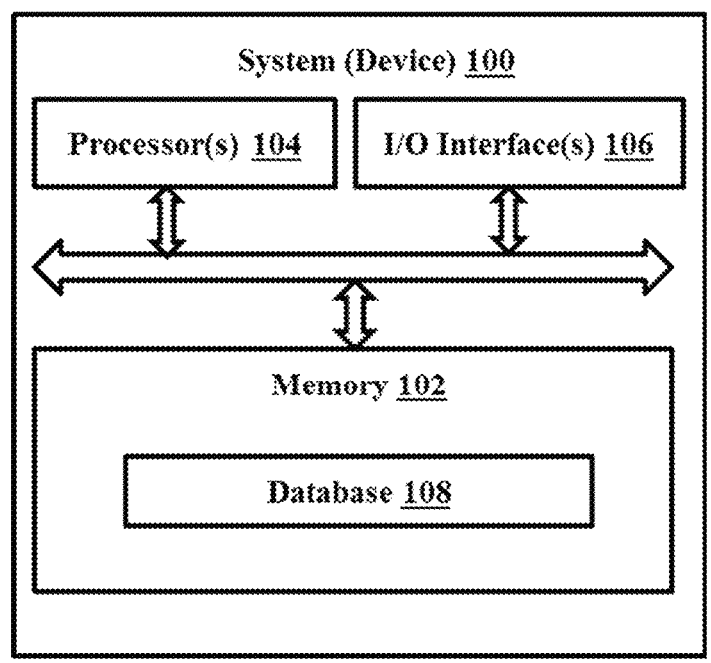
FIG. 1 is a functional block diagram of a system, interchangeably referred as device, for capacitive touch panel based biosignal measurement, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Embodiments herein provide a method and system for capacitive touch panel based biosignal measurement. Throughout the description, the system herein is interchangeably referred as device. The method senses a change in raw capacitance value ($\delta C$) of a capacitive touch panel of a device comprising an array of sensors. However, unlike existing methods that directly utilize the raw signal for biosignal measurements, the method disclosed herein derives a normalized signal by normalizing the raw signal corresponding to the change in raw capacitance ($\delta C$) of the capacitive touch panel. The normalization of the raw signal enables capturing inter-relationships between a plurality of variables that affect the raw capacitance value such as a) a set of device specific parameters associated with the capacitive touch panel of the device, b) a set of ethnographic parameters, and c) metadata associated with a subject been monitored. Thus, method provides correction in the raw signal before extracting one or more parameters of a primary biosignal, such as a Photoplethysmogram (PPG) and provides higher accuracy in biosignal measurement using capacitive touch panel based devices by personalizing the biosignal measurements. The method further enables deriving one or more parameters of one or more secondary biosignals.

The method attempts eliminating introduction of error in biosignal measurement due to specific characteristics of the capacitive touch panel been used by any device used for measurement, this enables providing device parameter agnostic biosignal measurements. Once the one or more parameters of the primary biosignal and/or the one or more secondary biosignals are derived, these are analyzed to generate health condition alerts to the subject and can be shared over a communication channel, such as internet, for an expert analysis.

Referring now to the drawings, and more particularly to FIGS. 1 through 7B, where similar reference characters denote corresponding features consistently throughout the figures, there are shown preferred embodiments and these embodiments are described in the context of the following exemplary system and/or method.

FIG. 1 is a functional block diagram of a system 100, alternatively referred as device 100, for capacitive touch panel based biosignal measurement, in accordance with some embodiments of the present disclosure. The system 100 herein, may be interchangeably referred as device 100.

In an embodiment, the system 100 includes a processor(s) 104, communication interface device(s), alternatively referred as input/output (I/O) interface(s) 106, and one or more data storage devices or a memory 102 operatively coupled to the processor(s) 104. In an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 is configured to fetch and execute computer-readable instructions stored in the memory 102. In an embodiment, the system 100 or device 100 can be implemented in a variety of computing systems that provide a capacitive touch panel interface, such as laptop computers, notebooks, hand-held devices such as mobile phones, workstations, mainframe computers, servers, a network cloud and the like.

The I/O interface(s) 106 can include a variety of software and hardware interfaces, for example, a web interface, a graphical user interface, a touch user interface (TUI) and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices to one another or to another server. The I/O interface 106, via the TUI, typically the capacitive touch panel, enables detecting a touch event performed by the subject on the capacitive touch panel of the device 100. The capacitive touch panel comprises an array of sensors, wherein the array is scanned at regular predefined time interval to obtain a raw signal corresponding to change in raw capacitance value ($\delta C$) generated by the capacitive touch panel due to the touch event. The sensed and scanned signal data can be stored in a database 108 of the memory 102. Further, one or more normalization models can be locally stored in the database, so as to enable the device 100 to utilize the appropriate best suitable normalization model for implementing the method for personalized biosignal measurement. Various statistical techniques and Machine learning (ML) techniques can also be stored in the repository, to be used for generating normalization models. Further, while generating the normalization models a set of changes in the raw capacitance values ($\delta Cs$) generated for a set of touch events performed by a set of sample subjects on a set of sample capacitive touch panels (representing the set of device specific parameters) along with corresponding set of ethnographic parameters and metadata of the set of sample subjects can also be stored in the database 108. Alternatively, these normalization models can be generated by a central server and stored in an external repository, to be accessed by the device. Further, the central server with incremental updates provides easy and scalable mechanism to update local database on the device 100. Also, true measurements of primary biosignal for the set of sample subjects and any subject under test and may be stored in the memory 102.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Thus, the memory 102 may comprise information pertaining to input(s)/output(s) of each step performed by the processor(s) 104 of the system 100 and methods of the present disclosure. Functions of the components of system 100 or the device 100 are explained in conjunction with method steps of flow diagram depicted in FIG. 2A, through FIG. 4.

Figure 2A:
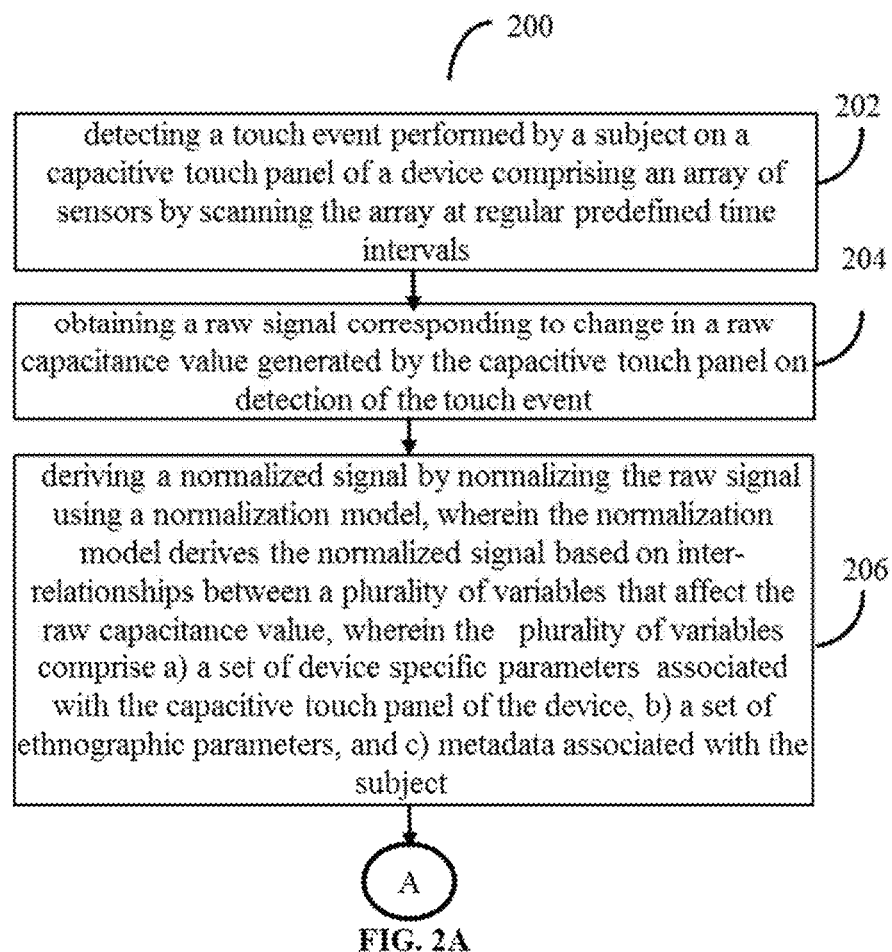
FIG. 2A and FIG. 2B is a flow diagram illustrating a method for capacitive touch panel based biosignal measurement, using the system of FIG. 1, in accordance with some embodiments of the present disclosure.
Figure 2B:
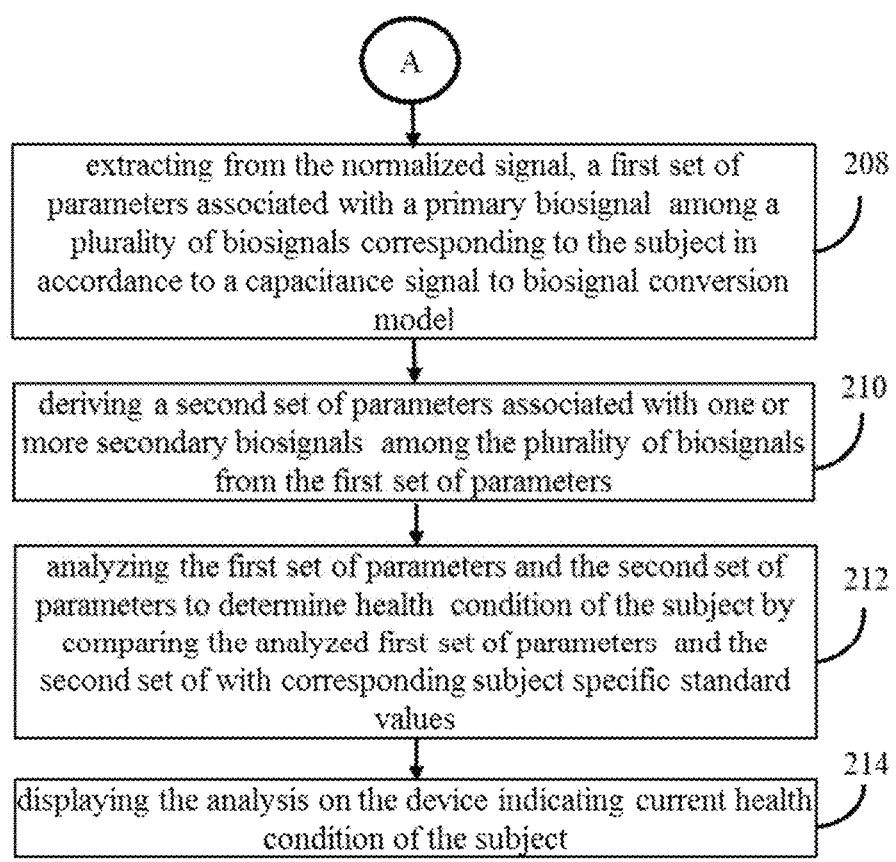

FIG. 2A and FIG. 2B depict a flow diagram of a method for capacitive touch panel based biosignal measurement, using the system of FIG. 1, in accordance with some embodiments of the present disclosure.

Figure 3:
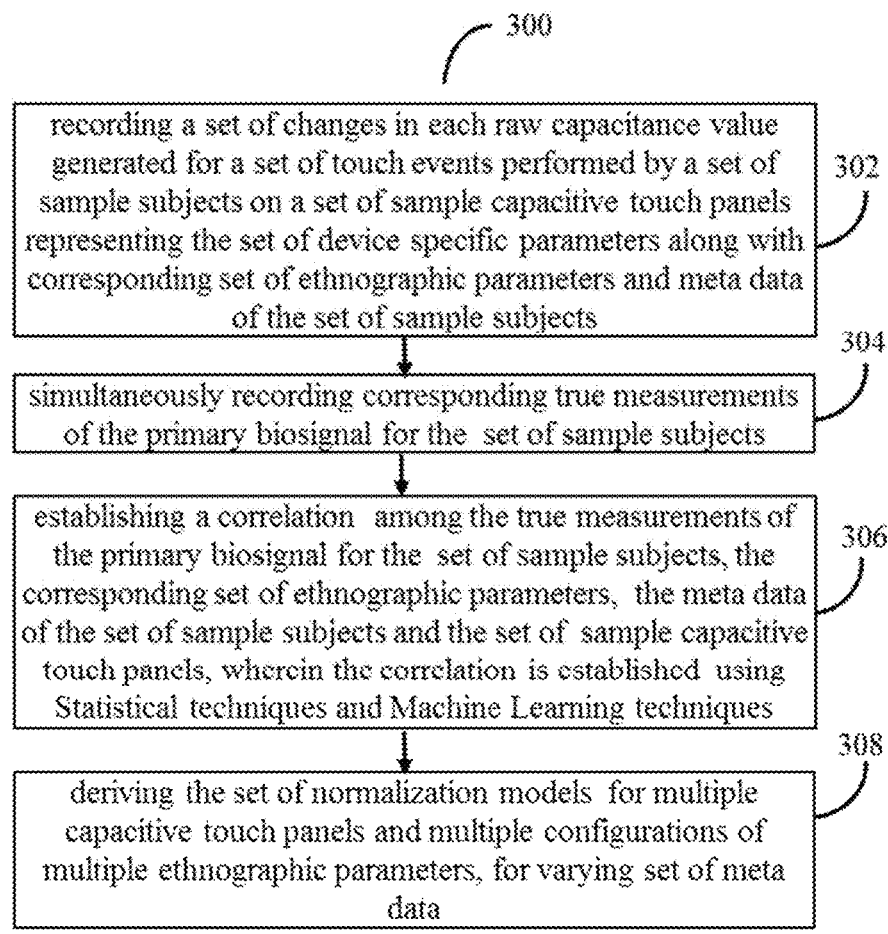
FIG. 3 illustrates a flow diagram depicting a process of the method of FIG. 2 for generating normalization models using a combination of statistical techniques and Machine Learning (ML) techniques implemented via the system of FIG. 1, in accordance with some embodiments of the present disclosure.
Figure 4:
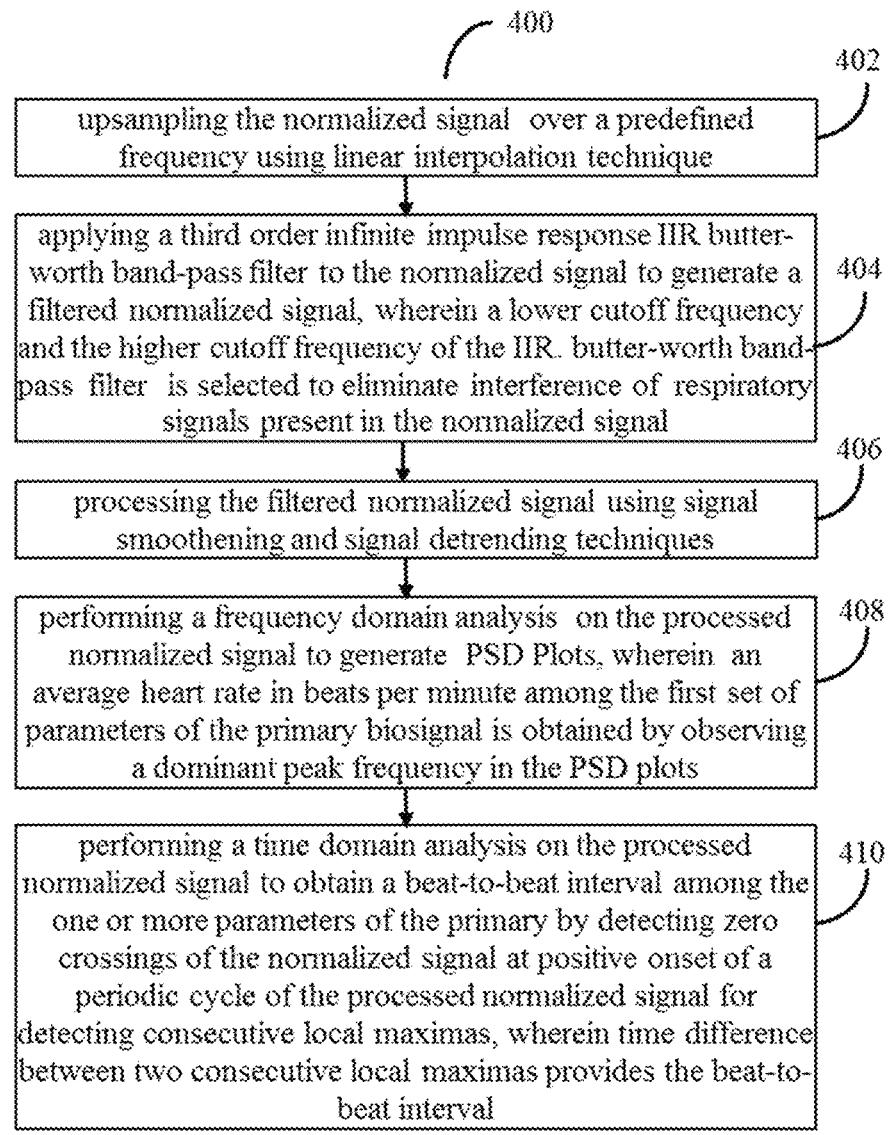
FIG. 4 illustrates a flow diagram depicting a process of the method of FIG. 2 for extracting one or more parameters of the primary bio signal from the normalized signal implemented via the system of FIG. 1, in accordance with some embodiments of the present disclosure.

In an embodiment, the system 100 comprises one or more data storage devices or the memory 102 operatively coupled to the processor(s) 104 and is configured to store instructions for execution of steps of the method 200 by the processor(s) 104. The steps of the method 200 of the present disclosure will now be explained with reference to the components or blocks of the system 100 as depicted in FIG. 1 and the steps of flow diagram as depicted in FIG. 2 through FIG. 4. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Figure 5A:
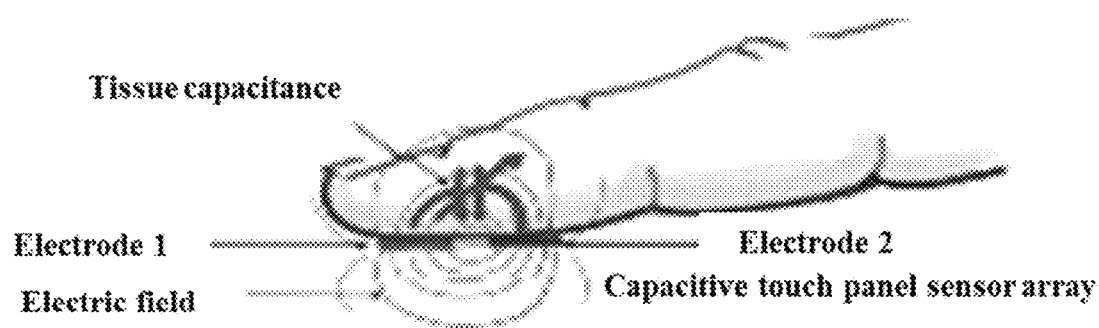
FIG. 5A depicts touch event on a capacitive touch panel of the system of FIG. 1, in accordance with some embodiments of the present disclosure.

Referring to the steps of the method 200, at step 202, the one or more hardware processors 104 are configured to detect a touch event performed by the subject on the capacitive touch panel of the device 100, wherein the capacitive touch panel comprises an array of sensors. The array of sensors is scanned at regular predefined time intervals. A representative arrangement of the sensor array and the touch event generated by a finger of the subject is depicted in FIG. 5A. On detection of the touch event, at step 204 of the method 200, the one or more hardware processors 104 are configured to obtain the raw signal corresponding to change in a raw capacitance ($\delta C$) value generated by the capacitive touch panel. As can be understood, the raw signal generated by touch panels of any device may not be readily accessible for any direct usage, as such access is restricted by device manufacturers. However, with support from the device specific manufacturers, the system 100 can have device specific drivers built in, which enable capturing the raw signals from the capacitive touch panels of devices for any further usage, such as biosignal measurements. The device specific drivers of the method 200 are based on valid touch, detected in accordance a predefined threshold capacitance level. As mentioned, the raw signal so obtained, however if directly used for biosignal measurement is prone to errors. Thus, at step 206 of the method 200, the one or more processors 104 are configured to derive a normalized signal by normalizing the raw signal. The normalization is performed using a normalization model comprised in the memory 102 or database 108, wherein the normalization model which when executed by the one or more hardware processors 104 derives the normalized signal by considering inter-relationships between the plurality of variables that affect the raw capacitance value. The plurality of variables comprises a) the set of device specific parameters associated with the capacitive touch panel of the device, b) the set of ethnographic parameters, and c) the metadata associated with the subject.

FIG. 3 illustrates a flow diagram depicting a process 300 for generating normalization models using a combination of statistical techniques and ML techniques implemented with reference to system of FIG. 1 and the method 200 of FIG. 2, in accordance with some embodiments of the present disclosure. The normalization models can be created by the system 100 apriori and stored in the database 108 or an external database, wherein specific normalization model best suited for a particular device and a specific subject can be accessed and used. Alternatively, these normalization models can be generated by a central server and stored in an external repository, to be accessed by the device through the I/O interface 106 via any of the available communication channels. Thus, for example, a client application on the device 100 can have the above mentioned set of models embedded in application or downloaded in real time. Client application can choose right set of normalization factor by a) getting the device display configuration, which provides characteristics of the capacitive touch panel and b) the metadata.

Referring now to the steps of process 300, at step 302, the one or more hardware processors 104 are configured to record the set of changes in the raw capacitance values ($\delta$Cs) generated for the set of touch events performed by the set of sample subjects on the set of sample capacitive touch panels representing the set of device specific parameters, along with corresponding set of ethnographic parameters and metadata of the set of sample subjects. The device specific parameters, the ethnographic parameters and the metadata represents the variables for generating the normalization models. For example, variable V1 through V3, among possible n variables (V1 through Vn), which may affect the change in capacitance represented by the raw signal may be:
  a) Capacitive touch panel (V1): Device parameters such as capacitive sensing elements density, dynamic range of change in capacitance value with respect to a touch event, delay in scanning the capacitance array, which is dependent on the processing power/speed of touch pad controller unit etc.
  b) Ethnographic parameters (V2): Includes average size of fingers, normalized static potential, skin color, dermal thickness etc.
  c) Users metadata (V3): Includes age, profession etc. For example, profession can affect the skin type, wherein farmers/machine operators might have thick dermal layers. Further medications such as diuretic drugs make skin dry.

An example implementation with modules for generating and utilizing the normalization module is provided below:
  a) Capacitive touch panel data collection module: This module queries operating system of the device (such as mobile phone) and obtains the required parameters of the capacitive touch panel. In case some of them are not programmatically available, they can be obtained from the technical specification of corresponding touch panel controller of the device.
  b) Capacitance variance ($\delta$C) collection module: This module or queries the touch pad controller and obtains the change in capacitance values ($\delta$Cs). Kernel level modification in the driver of display controller could be done in case the desired function is not readily available.
  c) Reference data collection module: This module can connect with medical grade biosignals measurement devices like ECG/PPG or the like and feed it to normalized model extraction module, capturing true measurements, to be used as reference data (Rd).
  d) Normalized model extraction module: This module can have a suite of statistical processing algorithms and machine learning frameworks. This module gives finite set of correlation between $\delta$C and (Vn, Rd) as output(s). For example, for logical grouping parameters within V1 within finite set by approximation. Typical value is a set of 5 groups. Same is done for V2 and V3 so that the number of input variables are limited without impacting significantly on the final accuracy of output model.

For end users: application: It is like #h file in C. V1 is obtained by querying the model/make/API calls by application itself. V2 could be derived from location by application itself. V3 could be obtained by asking end user to key in the data. Based on V1/V2/V3—appropriate model will be selected/downloaded from repository by client application for data analysis.

At step 304, the one or more hardware processors 104 are configured to simultaneously record corresponding true measurements of the primary biosignal for the set of sample subjects. An example data collection setup comprises a) Unit to collect the change in capacitance values ($\delta$Cs), users' metadata and the like and b) Unit comprising medically approved devices to collect corresponding biosignal (HR/BR) in parallel with ($\delta$Cs). Once the data is collected, at step 306, the one or more hardware processors 104 are configured to establish a correlation among the true measurements of the primary signal for the set of sample subjects, the corresponding set of ethnographic parameters, the metadata of the set of sample subjects and the set of sample capacitive touch panels. Establishing correlation refers to identifying a set of features among a plurality of features of the collected data using known statistical techniques for dimensionality reduction and then using ML techniques such as linear regression models and Support Vector Machine (SVM) models for regression and classification of the collected data. Further, at step 308, the one or more hardware processors 104 are configured to derive the set of normalization models for multiple capacitive touch panels and multiple configurations of multiple ethnographic parameters, for varying set of metadata.

Upon obtaining the normalized signal in accordance with the normalized model, which is appropriately selected for the device or system 100, referring back to step 208 of the method 200, the one or more hardware processors 104 are configured to extract, from the normalized signal, one or more parameters (say a first set of parameters) associated with the primary biosignal among a plurality of biosignals corresponding to the subject. The extraction is in accordance to a capacitance signal to biosignal conversion model. For example, from the primary biosignal, which can be a PPG signal, the one or more extracted parameters can be heart rate, pulse rate and the like.

Once the one or more parameters are extracted from the primary biosignal, at step 210 of the method 200, the one or more hardware processors 104 are configured to derive one or more parameters (say a second set of parameters) associated with one or more secondary biosignals. For example, the primary biosignal a longitudinal HR measurement is extracted and a derived or extracted one or more parameters of the secondary biosignal from the HR measurement can be heart rate variability (HRV). It can be done by logging HR data for extended period of time and using statistical techniques coupled with region specific medical standard guidelines to measure the HRV. Further, combination one or more parameters associated with PPG and ECG signals can enable deriving Blood pressure information of the subject. At step 212 of the method 200, the one or more hardware processors 104 are configured to analyze the one or more parameters (the first set of parameters) associated with the primary biosignal and the one or more parameters (the second set of parameters) associated with the secondary biosignals to determine health condition of the subject by comparing the analyzed one or more parameters with corresponding subject specific standard values. It can be noted that, subject specific standard values enable analyzing the subject in accordance with normal range values for specific health category of that subject and avoids raising unnecessary alerts. For example, patient taking certain types of medication could have elevated heart rate. Or some aged people have elevated blood pressure—which is normal for their condition.

Further, at step 214 of the method 200, the one or more hardware processors 104 are configured to display the analysis on the device indicating current health condition of the subject.

FIG. 4 illustrates a flow diagram 400 depicting a process of the method of FIG. 2 with reference to the system 100 for extracting one or more parameters of the primary bio signal from the normalized signal, in accordance with some embodiments of the present disclosure. At step 402 of the process 400, the one or more hardware processors 104 are configured to upsample the normalized signal over a predefined frequency using linear interpolation technique. At step 404 of the process 400, the one or more hardware processors 104 are configured to apply a third order infinite impulse response IIR Butterworth band-pass filter to the normalized signal to generate a filtered normalized signal, wherein a lower cutoff frequency and a higher cutoff frequency of the IIR Butter-worth band-pass filter is selected to eliminate interference of respiratory signals present in the normalized signal. At step 406 of the process 400, the one or more hardware processors are configured to process the filtered normalized signal using signal smoothening and signal detrending techniques. At step 408 of the process 400, the one or more hardware processors are configured to perform a frequency domain analysis on the processed normalized signal to generate Power Spectral Density (PSD) Plots. An average heart rate in beats per minute among the one or more parameters of the primary biosignal is obtained by observing a dominant peak frequency in the PSD. At step 410 of the process 400, the one or more hardware processors are configured to perform a time domain analysis on the processed normalized signal to obtain a beat-to-beat interval among the one or more parameters of the primary. The beat-to-beat interval can be obtained by detecting zero crossings of the processed normalized signal at positive onset of a periodic cycle of the normalized signal for detecting consecutive local maximas, wherein time difference between two consecutive local maximas provides the beat-to-beat interval.

Experimental Results for Validating Accuracy of One or More Parameters Estimated from the Change in Capacitance of the Capacitive Touch Panel and True Measurement of a Biosignal Such as a PPG Signal (Cardiac Signal) Obtained from Standard Clinical Measurements Six trails from different age groups participated in the experiment to validate the results. The results discuss on a) evaluation of the mean heart rate in the frequency domain and its corresponding absolute error measurements in beats per minute (B.P.M.) and b) M.A.E. beat-to-beat heart rate (H.R.) measurement in the time domain. The participants are requested to sit on a chair in front of a capacitive touch sensor or capacitive touch panel such as available from Texas Inc. The capacitive touch sensors have a sampling rate of 20 Hz. The pulse oximeter serving as a reference instrument to capture PPG signal and having a sampling rate of 60 Hz is clipped into the middle finger of each participant in every trial. The corresponding participant is then asked to touch the two electrodes in the sensor board using one of their fingertips from the other hand. The arrangement is as shown in FIG. 5A. The participants were then asked to try and apply similar amount of pressure at the fingertip touching the sensors and breathe normally. They were also requested to keep their finger steady while touching the sensors in order to minimize sudden abrupt change in capacitance values due to body movement artifacts. The experimental data from the reference instrument and the capacitive sensors is simultaneously recorded for 30 seconds and safely stored in the system 100 to be later processed in MATLAB™. Each participant is requested to undergo physical exercise to increase their heart rate. This is carried out to test the accuracy and validate findings for a higher pulse rate estimation. Experimental data for a higher heart rate are recorded in the same manner as that of the normal heart rate.

Figure 5B:
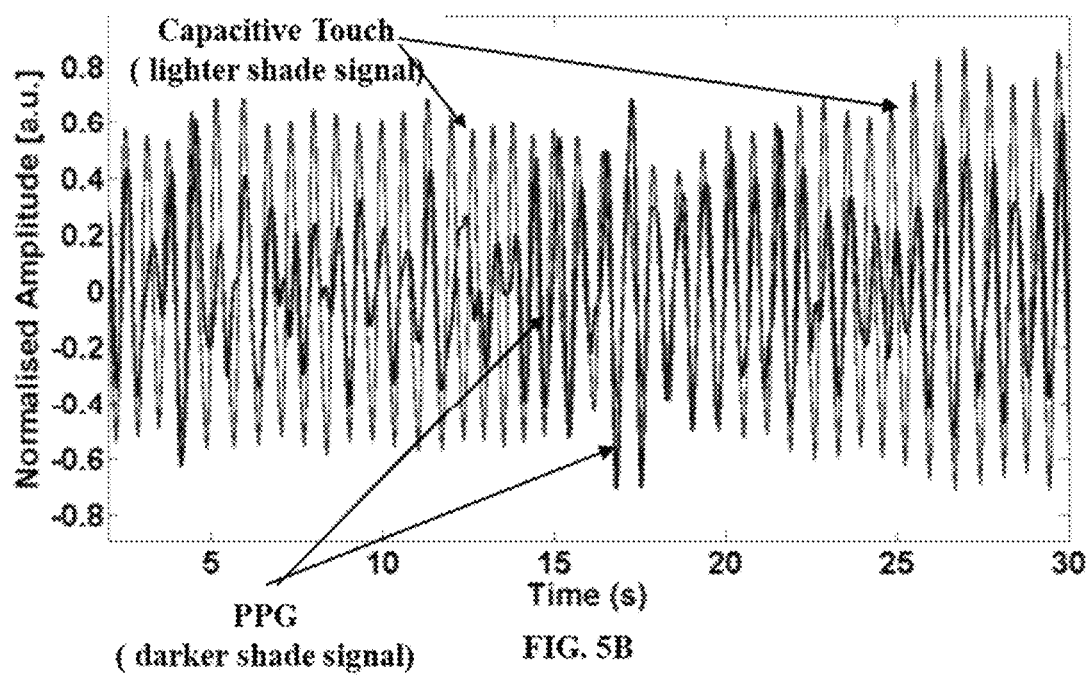
FIG. 5B depicts synchronized signals comprising a normalized signal sensed at the capacitive touch panel and a true measurement of a Photoplethysmogram (PPG) signal, in accordance with some embodiments of the present disclosure.

A. Heart Rate Extraction: The signals obtained from the sensor board and the reference instrument are upsampled over 250 Hz using linear interpolation. This is done to ensure that the recommended bandwidth of 250 Hz while dealing with heart rate measurements is maintained. The sampling frequency used by the method disclosed herein was upheld at 256 Hz. The third order infinite impulse response (I.I.R.) butter-worth band-pass digital filter is applied to the signals of our interest to extract the heart rate. The cut-off frequencies were chosen to be 0.8-3 Hz, thereby covering a heart rate of almost 50-180 Beats per Minute (B.P.M). The lower cut-off frequency was set at 0.8. Hz. This is to ensure that the respiratory signals (having a bandwidth of 0.1-0.5 Hz) does not interfere with the cardiac signals. The higher cut-off frequency was set to 3 Hz to cover a realistic heart rate of 180 beats per minute. The filtered signals are later smoothed at the edges and also de-trended to remove any baseline wandering. FIG. 5B depicts plots of the normalized filtered signal obtained from the sensors and the reference instrument. Tests are carried out for 30 seconds from Trail No. 2 undergoing normal heart rate measurements. The filtered signals were then later analyzed in the frequency and time domain to estimate the mean heart rate.

B. Frequency Domain Analysis: The Power Spectral Density Plots (P.S.D.) were used to determine the heart rate in the frequency domain. PSD plots were very useful in comparing the similarity of the signals that are obtained from the experimental trials. The similarity can be analyzed in terms of signal classification, detection or even periodicity by observing the dominant peak frequency in a PSD plot as described in literature. Therefore, normalized overlapping PSD curves are plotted to analyze the similarity of the PPG signal and the signal obtained due to the change in the dielectric property of the finger touching the two electrodes. The mean heart rate can be extracted by carefully detecting the dominant peak frequency. The PPG signal was used as a reference signal to validate the average pulse rate due to its wide acceptance in the modern healthcare centers.

C. Time Domain Analysis: There are different approaches in the time domain to measure the beat-to-beat heart rate. One of the approaches in literature was utilized to predict the beat-to-beat pulse rate by first identifying the zero crossing points on the signals of interest. The zero crossing points helps to determine the onset of each heartbeat. The positive value at the onset of each heart beat can be expressed as:

$$i:\{y_i, y \geq 0\}$$

$$\{y_i, y < 0\} \quad (1)$$

where, the signal value at a given time index i is expressed as y. Then, the local maximum points and the time indices between two consecutive onset heartbeat can be mathematically expressed as:

$$\forall y \in [a,b], f(y) \geq f(Y) \quad (2)$$

where, a and b correspond to the two consecutive heart beats at the positive onset of a cycle and the local maximum signal of a heart cycle is given by Y. The difference in time interval between the two consecutive maxima points (TRi) was calculated to give the duration of each $i^{th}$ beat. Eventually, $i^{th}$ beat to beat heart rate can be calculated as TRi/60. The beat-to-beat heart rate obtained from the reference instrument is compared to the measured beat-to-beat heart rate from the change in capacitance values varying over time. The accuracy and the performance standard of this method to measure the heart rate in beats per minute is governed in terms of the absolute mean error (MAE), which is given by:

$$MAE = \frac{1}{n} \sum_{i=1}^{n} |f_h(i) - f_h'(i)| \quad (3)$$

where, $f_h$ and $f_h'$ represent the average heart rate obtained from the reference instrument and the method of the present disclosure respectively. The total number of beats considered for each volunteer in the trail are represented by n.

Results and Discussion:

The filtered signal from the sensor board is compared with the reference signal, recorded from the pulse oximeter. Tests and measurements are carried out in the time and frequency domain to validate the results.

A. Frequency Domain Measurement: Normalized PSD curves are plotted for each and every trail in the frequency domain. The average heart rate in beats per minute is obtained by observing the dominant peak frequency. Normal and fast heart rate conditions in beats per minute for each trail is reported in Table I.

TABLE I

| Trail No | Normal heart rate | | Fast heart rate (B.P.M) | |
|---|---|---|---|---|
| | Reference Heart Rate | Fixed Heart Rate | Reference Heart Rate | Fixed Heart Rate |
| 1 | 84.24 | 84.24 | 89.40 | 89.40 |
| 2 | 58.08 | 57.60 | 60.60 | 60.60 |
| 3 | 66.60 | 66.60 | 71.88 | 71.40 |
| 4 | 76.62 | 74.28 | 81.90 | 83.76 |

TABLE I-continued

| Trail No | Normal heart rate | | Fast heart rate (B.P.M) | |
|---|---|---|---|---|
| | Reference Heart Rate | Fixed Heart Rate | Reference Heart Rate | Fixed Heart Rate |
| 5 | 71.40 | 70.92 | 78.54 | 74.76 |
| 6 | 66.60 | 72.60 | 68.10 | 66.60 |

Figure 6:
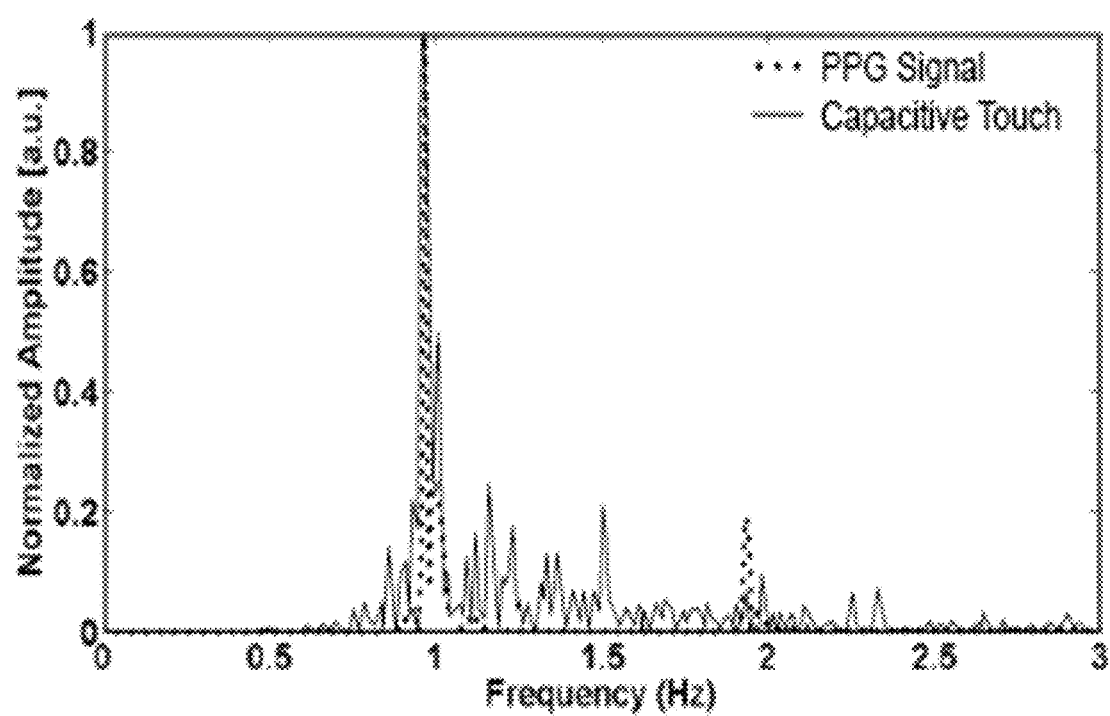
FIG. 6, FIG. 7A and FIG. 7B depict overlapped Power Spectral Density (PSD) Plots PSD plots of the normalized signal and the PPG signal at various heart rate conditions, in accordance with some embodiments of the present disclosure.
Figure 7A:
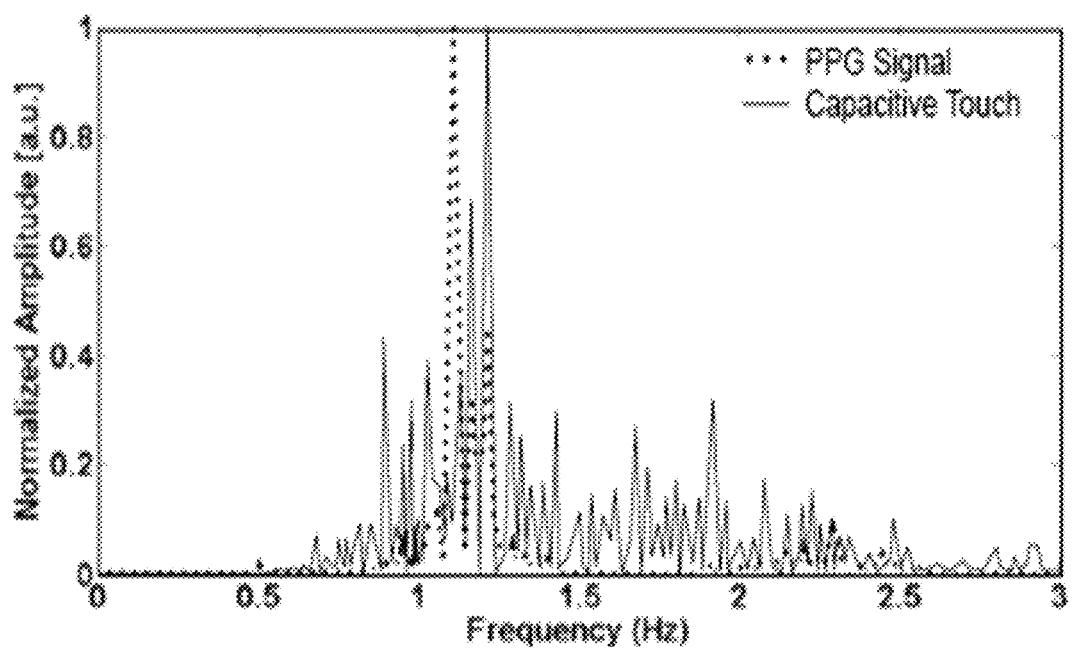
Figure 7B:
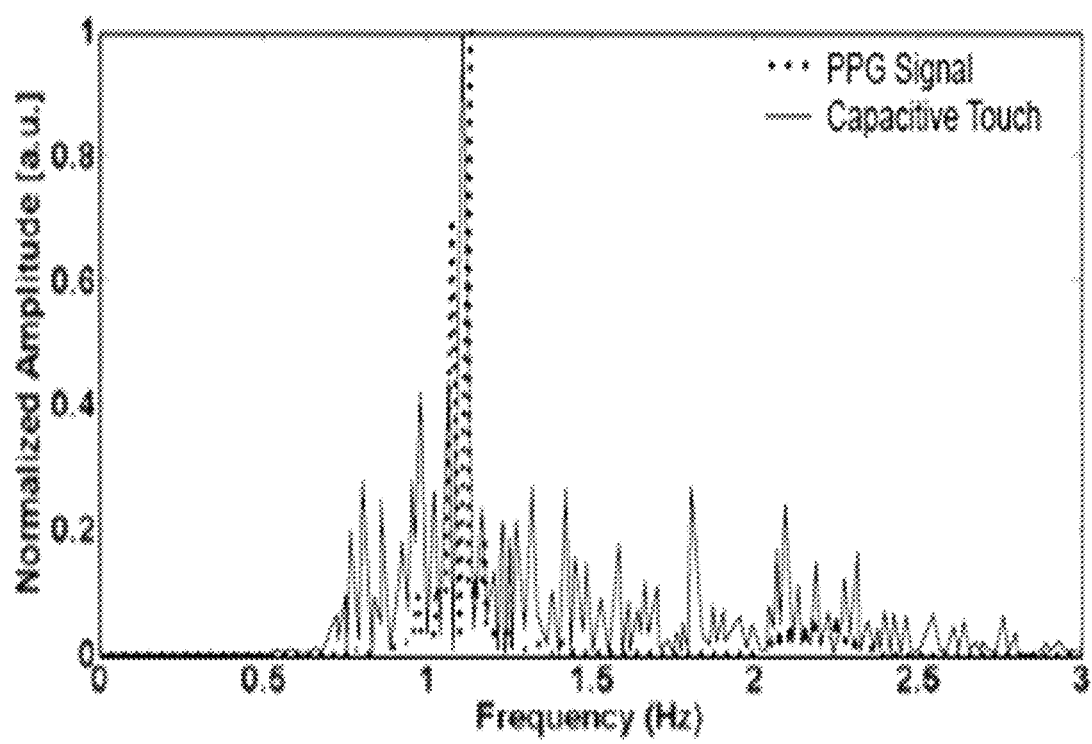

Observing Table I, it can be concluded that the mean heart rate measurements (normal and fast heart rate) in the frequency domain is accurate and the error percentage for almost all the measurements is below 5%. It is also noteworthy to mention that the accuracy for some trails is reported to be 100%. The absolute error percentage for Trail No. 6 is 9% and is reported to be the highest among all the trails. The reason for failing to accurately identify the dominant peak frequency is because the capacitive touch sensors are highly sensitive to body movements. This seems to be the case with the Trail No. 6 undergoing normal heart rate measurements. Nonetheless, the absolute error percentage is well below 5% for the same trail undergoing fast heart rate measurements. This is shown in FIGS. 7A and 7B. Overlapping PSD curves for Trail No. 2 undergoing normal heart rate conditions are shown in FIG. 6. Examining FIG. 6, the capacitive touch traces the PPG signal with the dominant peaks appearing almost in the same frequency in the PSD curve.

B. Time Domain Measurements: Continuous monitoring of the vital signs, like that of the heart rate, is very useful in clinical arrangements. Therefore, obtaining the beat-to-beat heart rate is very crucial in monitoring patient's overall health conditions. The frequency domain analysis using the PSD curves solely helps us in estimating the mean heart rate over a period of time. Hence, the time domain analysis is performed to monitor the beat-to-beat heart rate. Table II presents the beat-to-beat heart rate performance in terms of Mean Absolute Error (MAE). Examining Table II, it is noteworthy to mention that the MAE is considerably higher for trails with higher heart rate after performing some physical exercise. This is mainly because of the motion artefacts that have been introduced into the recorded signals. The average MAE is reported to be 3.83 beats·min-1 for all the trails in their normal heart rate conditions

TABLE II

| Trail No | MAE Normal heart rate B.P.M | MAE Fixed heart rate B.P.M |
|---|---|---|
| 1 | 6.05 | 12.08 |
| 2 | 0.177 | 6.04 |
| 3 | 3.39 | 7.56 |
| 4 | 7.28 | 14.72 |
| 5 | 3.1 | 5.07 |
| 6 | 3.02 | 6.07 |

Even though the description explicitly refers to PPG as the primary biosignal, with minimal modifications to approach discussed by the method disclosed herein, one or more parameters related to ECG, GSR and the like can be obtained.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for capacitive touch panel based bio-signal measurement, the method comprising:

detecting, via one or more hardware processors, a touch event performed by a subject on a capacitive touch panel of a device comprising an array of sensors by scanning the array at regular predefined time intervals;

obtaining, via the one or more hardware processors, a raw signal corresponding to change in a raw capacitance value generated by the capacitive touch panel on detection of the touch event;

deriving, via the one or more hardware processors, a normalized signal by normalizing the raw signal using a normalization model, wherein the normalization model derives the normalized signal based on inter-relationships between a plurality of variables that affect the raw capacitance value, wherein the plurality of variables comprise a) a set of device specific parameters associated with the capacitive touch panel of the device, b) a set of ethnographic parameters, and c) metadata associated with the subject, wherein the set of device specific parameters comprises capacitive sensing elements density, dynamic range of change in the capacitance value with respect to the touch event, and delay in scanning capacitance array, which is dependent on processing power/speed of touch pad controller unit; wherein the set of ethnographic parameters comprises average size of fingers, normalized static potential, skin color and dermal thickness; wherein the metadata associated with the subject includes age and profession; and wherein the normalization model is generated using a combination of statistical techniques and Machine Learning (ML), techniques, wherein the normalization model is generated by a central server and stored in an external repository to be accessed by the device, wherein the generation comprises:

recording a set of changes in each raw capacitance value generated for a set of touch events performed by a set of sample subjects on a set of sample capacitive touch panels, representing the set of device specific parameters, along with a corresponding set of ethnographic parameters and metadata of the set of sample subjects, wherein the set of device specific parameters, the set of ethnographic parameters and the metadata associated with the subject represents the plurality of variables for generating the normalization model;

simultaneously recording corresponding true measurements of a primary biosignal for the set of sample subjects;

establishing a correlation among the true measurements of the primary biosignal for the set of sample subjects, the corresponding set of ethnographic parameters, the metadata of the set of sample subjects and the set of sample capacitive touch panels, wherein the correlation is established using the statistical techniques and the ML techniques; and deriving a set of normalization models from a plurality of normalization models for multiple capacitive touch panels and multiple configurations of multiple ethnographic parameters, for a varying set of metadata;

extracting, via the one or more hardware processors, from the normalized signal, a first set of parameters associated with the primary biosignal among a plurality of biosignals corresponding to the subject in accordance with a capacitance signal to a biosignal conversion model, wherein the first set of parameters comprise heart rate and pulse rate;

deriving, via the one or more hardware processors, a second set of parameters associated with one or more secondary biosignals among the plurality of biosignals from the first set of parameters associated with the primary biosignal, wherein the second set of parameters comprise heart rate variability;

analyzing, via the one or more hardware processors, the first set of parameters associated with the primary biosignal, and the second set of parameters associated with the secondary biosignals to generate an alert indicative of health condition of the subject by comparing the analyzed first set of parameters and the second set of parameters with corresponding subject specific standard values; and displaying, via the one or more hardware processors, the analysis on the device indicating current health condition of the subject.

2. The method of claim 1, wherein the normalization model is pre-selected in accordance with the device and the subject from the set of normalization models from the plurality of normalization models stored in a repository.

3. The method of claim 1, wherein the step of extracting one or more parameters of the primary biosignal from the normalized signal comprises:

upsampling the normalized signal over a predefined frequency using linear interpolation technique;

applying a third order infinite impulse response (IIR) Butterworth band-pass filter to the normalized signal to generate a filtered normalized signal, wherein a lower cutoff frequency and a higher cutoff frequency of the IIR Butter-worth band-pass filter are selected to eliminate interference of respiratory signals present in the normalized signal;

processing the filtered normalized signal using signal smoothening and signal detrending techniques; and performing:

a frequency domain analysis on the processed normalized signal to generate Power Spectral Density (PSD) Plots, wherein an average heart rate in beats per minute among the first set of parameters of the primary biosignal is obtained by observing a dominant peak frequency in the PSD plots; and a time domain analysis on the processed normalized signal to obtain a beat-to-beat interval among the one or more parameters of the primary biosignal by detecting zero crossings of the processed normalized signal at positive onset of a periodic cycle of the processed normalized signal for detecting consecutive local maximas, wherein time difference between two consecutives local maximas provides a beat-to-beat interval.

4. A device for capacitive touch panel based biosignal measurement, the device comprising:

a memory storing instructions;

one or more Input/Output (I/O) interfaces; and one or more hardware processors coupled to the memory via the one or more I/O interfaces, wherein the one or more hardware processors are configured by the instructions to:

detect a touch event performed by a subject on a capacitive touch panel of a device comprising an array of sensors by scanning the array at regular predefined time intervals;

obtain a raw signal corresponding to change in a raw capacitance value generated by the capacitive touch panel on detection of the touch event;

derive a normalized signal by normalizing the raw signal using a normalization model, wherein the normalization model derives the normalized signal based on inter-relationships between a plurality of variables that affect the raw capacitance value, wherein the plurality of variables comprise a) a set of device specific parameters associated with the capacitive touch panel of the device, b) a set of ethnographic parameters, and c) metadata associated with the subject, wherein the set of device specific parameters comprises capacitive sensing elements density, dynamic range of change in the capacitance value with respect to the touch event, and delay in scanning capacitance array, which is dependent on processing power/speed of touch pad controller unit; wherein the set of ethnographic parameters comprises average size of fingers, normalized static potential, skin color and dermal thickness; wherein the metadata associated with the subject includes age and profession; and wherein the normalization model generated using a combination of statistical techniques and Machine Learning (ML), techniques, wherein the normalization model is generated by a central server and stored in an external repository to be accessed by the device, wherein the generation comprises:

recording a set of changes in each raw capacitance value generated for a set of touch events performed by a set of sample subjects on a set of sample capacitive touch panels, representing the set of device specific parameters, along with a corresponding set of ethnographic parameters and metadata of the set of sample subjects, wherein the set of device specific parameters, the set of ethnographic parameters and the metadata associated with the subject represents the plurality of variables for generating the normalization model;

simultaneously recording corresponding true measurements of a primary biosignal for the set of sample subjects;

establishing a correlation among the true measurements of the primary biosignal for the set of sample subjects, the corresponding set of ethnographic parameters, the metadata of the set of sample subjects and the set of sample capacitive touch panels, wherein the correlation is established using the statistical techniques and the ML techniques; and deriving a set of normalization models from a plurality of normalization models for multiple capacitive touch panels and multiple configurations of multiple ethnographic parameters, for a varying set of metadata;

extract from the normalized signal, a first set of parameters associated with the primary biosignal among a plurality of biosignals corresponding to the subject in accordance with a capacitance signal to a biosignal conversion model, wherein the first set of parameters comprise heart rate and pulse rate;

derive a second set of parameters associated with one or more secondary biosignals among the plurality of biosignals from the first set of parameters associated with the primary biosignal, wherein the second set of parameters comprise heart rate variability;

analyzing the first set of parameters associated with the primary biosignal and the second set of parameters associated with the secondary biosignals to generate an alert indicative of health condition of the subject by comparing the analyzed first set of parameters and the second set of parameters with corresponding subject specific standard values; and display analysis on the device indicating current health condition of the subject.

5. The device of claim 4, wherein the one or more hardware processors are configured to pre-select the normalization model in accordance with the device and the subject from the set of normalization models from the plurality of normalization models stored in a repository.

6. The device of claim 4, wherein the one or more hardware processors are configured to extract one or more parameters of the primary biosignal from the normalized signal by:

upsampling the normalized signal over a predefined frequency using linear interpolation technique;

applying a third order infinite impulse response (IIR) Butter-worth band-pass filter to the normalized signal to generate a filtered normalized signal, wherein a lower cutoff frequency and a higher cutoff frequency of the IIR Butter-worth band-pass filter are selected to eliminate interference of respiratory signals present in the normalized signal;

processing the filtered normalized signal using signal smoothening and signal detrending techniques; and performing:

a frequency domain analysis on the processed normalized signal to generate Power Spectral Density (PSD) Plots, wherein an average heart rate in beats per minute among the first set of parameters of the primary biosignal is obtained by observing a dominant peak frequency in the PSD plots; and a time domain analysis on the processed normalized signal to obtain a beat-to-beat interval among the first set of parameters of the primary biosignal by detecting zero crossings of the normalized signal at positive onset of a periodic cycle of the processed normalized signal for detecting consecutive local maximas, wherein time difference between two consecutives local maximas provides the beat-to-beat interval.

7. One or more non-transitory machine-readable information storage mediums comprising one or more instructions, which when executed by one or more hardware processors cause a method for:

detecting a touch event performed by a subject on a capacitive touch panel of a device comprising an array of sensors by scanning the array at regular predefined time intervals;

obtaining a raw signal corresponding to change in a raw capacitance value generated by the capacitive touch panel on detection of the touch event;

deriving a normalized signal by normalizing the raw signal using a normalization model, wherein the normalization model derives the normalized signal based on inter-relationships between a plurality of variables that affect the raw capacitance value, wherein the plurality of variables comprise a) a set of device specific parameters associated with the capacitive touch panel of the device, b) a set of ethnographic parameters, and c) metadata associated with the subject, wherein the set of device specific parameters comprises capacitive sensing elements density, dynamic range of change in the capacitance value with respect to the touch event, and delay in scanning capacitance array, which is dependent on processing power/speed of touch pad controller unit; wherein the set of ethnographic parameters comprises average size of fingers, normalized static potential, skin color and dermal thickness; wherein the metadata associated with the subject includes age and profession; and wherein the normalization model generated using a combination of statistical techniques and Machine Learning; (ML), techniques, wherein the normalization model is generated by a central server and stored in an external repository to be accessed by the device, wherein the generation comprises:

recording a set of changes in each raw capacitance value generated for a set of touch events performed by a set of sample subjects on a set of sample capacitive touch panels, representing the set of device specific parameters, along with a corresponding set of ethnographic parameters and metadata of the set of sample subjects, wherein the set of device specific parameters, the set of ethnographic parameters and the metadata associated with the subject represents the plurality of variables for generating the normalization model;

simultaneously recording corresponding true measurements of a primary biosignal for the set of sample subjects;

establishing a correlation among the true measurements of the primary biosignal for the set of sample subjects, the corresponding set of ethnographic parameters, the metadata of the set of sample subjects and the set of sample capacitive touch panels, wherein the correlation is established using the statistical techniques and the ML techniques; and deriving a set of normalization models from a plurality of normalization models for multiple capacitive touch panels and multiple configurations of multiple ethnographic parameters, for a varying set of metadata;

extracting from the normalized signal, a first set of parameters associated with the primary biosignal among a plurality of biosignals corresponding to the subject in accordance with a capacitance signal to a biosignal conversion model, wherein the first set of parameters comprise heart rate and pulse rate;

deriving a second set of parameters associated with one or more secondary biosignals among the plurality of biosignals from the first set of parameters associated with the primary biosignal, wherein the second set of parameters comprise heart rate variability;

analyzing the first set of parameters associated with the primary biosignal and the second set of parameters associated with the secondary biosignals to generate an alert indicative of health condition of the subject by comparing the analyzed first set of parameters and the second set of parameters with corresponding subject specific standard values; and displaying the analysis on the device indicating current health condition of the subject.

8. The one or more non-transitory machine-readable information storage mediums of claim 7, wherein the normalization model is pre-selected in accordance with the device and the subject from the set of normalization models from the plurality of normalization models stored in a repository.

9. The one or more non-transitory machine-readable information storage mediums of claim 7, wherein the step of extracting one or more parameters of the primary biosignal from the normalized signal comprises:

upsampling the normalized signal over a predefined frequency using linear interpolation technique;

applying a third order infinite impulse response (IIR) Butterworth band-pass filter to the normalized signal to generate a filtered normalized signal, wherein a lower cutoff frequency and a higher cutoff frequency of the IIR Butter-worth band-pass filter are selected to eliminate interference of respiratory signals present in the normalized signal;

processing the filtered normalized signal using signal smoothening and signal detrending techniques; and performing:

a frequency domain analysis on the processed normalized signal to generate Power Spectral Density (PSD) Plots, wherein an average heart rate in beats per minute among the first set of parameters of the primary biosignal is obtained by observing a dominant peak frequency in the PSD plots; and a time domain analysis on the processed normalized signal to obtain a beat-to-beat interval among the one or more parameters of the primary biosignal by detecting zero crossings of the processed normalized signal at positive onset of a periodic cycle of the processed normalized signal for detecting consecutive local maximas, wherein time difference between two consecutives local maximas provides a beat-to-beat interval.

\* \* \* \* \*